US008327726B2

(12) United States Patent
Kim et al.

(10) Patent No.: US 8,327,726 B2

(45) Date of Patent: Dec. 11, 2012

(54) MICROFLUIDIC DEVICE

(75) Inventors: Dogyoon Kim, Yongin-si (KR); Yoonkyoung Cho, Suwon-si (KR); Hansang Kim, Osan-si (KR); Yangui Lee, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 471 days.

(21) Appl. No.: 12/544,636

(22) Filed: Aug. 20, 2009

(65) Prior Publication Data

US 2010/0071486 A1 Mar. 25, 2010

(30) Foreign Application Priority Data

Sep. 23, 2008 (KR) ........................ 10-2008-0093372

(51) Int. Cl.

| | |
|---|---|
| ***G01N 1/00*** | (2006.01) |
| ***G01N 35/00*** | (2006.01) |
| ***G01N 9/30*** | (2006.01) |
| ***G01N 33/00*** | (2006.01) |
| ***B01L 3/00*** | (2006.01) |
| *C12M 3/00* | (2006.01) |
| *G01N 21/75* | (2006.01) |
| *F04B 19/00* | (2006.01) |
| *B01D 45/00* | (2006.01) |
| *F16K 3/00* | (2006.01) |

(52) U.S. Cl. ...... 73/864.81; 422/68.1; 422/72; 422/402; 422/415; 422/417; 422/502; 422/504; 422/506; 422/507; 422/533; 422/537; 436/45; 435/287.3; 435/288.5; 73/863; 73/64.56

(58) Field of Classification Search ........................ None

See application file for complete search history.

(56) References Cited

U.S. PATENT DOCUMENTS

| | | | | |
|---|---|---|---|---|
| 4,663,296 | A | 5/1987 | Revillet et al. | |
| 5,518,930 | A | 5/1996 | Burd | |
| 5,591,643 | A | 1/1997 | Schembri | |
| 5,693,233 | A | 12/1997 | Schembri | |
| 6,235,531 | B1 | 5/2001 | Kopf-Sill et al. | |
| 2002/0106786 | A1 | 8/2002 | Carvalho et al. | |
| 2003/0044322 | A1 * | 3/2003 | Andersson et al. | 422/100 |
| 2003/0207457 | A1 * | 11/2003 | Kopf-Sill et al. | 436/45 |
| 2004/0265172 | A1 * | 12/2004 | Pugia et al. | 422/58 |
| 2005/0130177 | A1 * | 6/2005 | Bedingham et al. | 435/6 |

(Continued)

FOREIGN PATENT DOCUMENTS

FR 2 575 293 A1 6/1986

(Continued)

*Primary Examiner* — In Suk Bullock

*Assistant Examiner* — Jennifer Wecker

(74) *Attorney, Agent, or Firm* — Sughrue Mion, PLLC

(57) ABSTRACT

A microfluidic device includes a sample chamber accommodating a sample, a first sample distribution unit connected to the sample chamber and receiving the sample, a sample transfer unit connected to the first sample distribution unit and forming a path for transferring the sample, and including a first connection unit connected to the first sample distribution unit and a second connection unit, wherein the distance from the center of rotation to the second connection unit is greater than the distance from the center of rotation to the first connection unit, a second sample distribution unit connected to the second connection unit and receiving the sample transferred via the sample transfer unit after filling the first sample distribution unit, and first and second analysis units respectively connected to the first and second sample distribution units and analyzing ingredients of the sample.

20 Claims, 7 Drawing Sheets

U.S. PATENT DOCUMENTS

2005/0136545 A1* 6/2005 Schmid et al. .................. 436/45
2007/0189927 A1* 8/2007 Ballhorn et al. ............. 422/68.1
2008/0056949 A1* 3/2008 Lee et al. ........................ 422/72
2009/0053108 A1* 2/2009 Cho et al. ........................ 422/72
2009/0238724 A1* 9/2009 Yamamoto et al. .......... 422/68.1

FOREIGN PATENT DOCUMENTS

WO WO 2007052648 A1 * 5/2007

* cited by examiner

MICROFLUIDIC DEVICE

CROSS-REFERENCE TO RELATED APPLICATIONS

This application claims priority from Korean Patent Application No. 10-2008-0093372, filed on Sep. 23, 2008 in the Korean Intellectual Property Office, the disclosure of which is incorporated herein in its entirety by reference.

BACKGROUND

1. Field

Apparatuses consistent with the present invention relate to a microfluidic device having a microfluidic structure for flowing a fluid to analyze an ingredient of a sample using a reaction between the sample and a reagent.

2. Description of the Related Art

A variety of methods for analyzing samples have been developed in various applied fields such as environmental monitoring, food tests, and medical diagnosis. Existing test methods require numerous manual operations and various apparatuses. To perform a test according to a predetermined protocol, an experienced tester needs to manually perform a variety of steps such as reagent loading, mixing, separation and movement, reactions, and centrifuges, several times. Therefore, errors may be easily generated when obtaining results of the test.

Accordingly, an experienced clinical pathologist is needed to quickly perform a test. However, even an experienced clinical pathologist has lots of difficulties in simultaneously performing various tests. For example, in the diagnosis of an urgent case, a quick test result is very important for performing quick emergency treatment. Thus, there is a demand for an apparatus capable of quickly and accurately performing various pathological tests needed according to various situations.

A large and expensive automated apparatus is used for a related art pathological test and a relatively large amount of a test material such as blood is required. Accordingly, a test result may be issued from as long as two days to two weeks after the test material is obtained from a patient.

To address this problem, a compact and automated apparatus has been developed which may quickly analyze a test material(s) obtained from one or more patients if necessary. For example, when blood is loaded in a disk type microfluidic device and the disk type microfluidic device is rotated, serum is separated from the blood due to a centrifugal force. The separated serum is mixed with a predetermined amount of dilution buffer and moved to a plurality of reaction chambers in the disk type microfluidic device. Different reagents are previously loaded in the reaction chambers for different blood test items so that the different reagents react to the serum to present a predetermined color. Blood analysis may be performed by detecting a change in the color.

SUMMARY

One or more embodiments include a microfluidic device capable of analyzing a sample in a plurality of analysis units using a sample loaded in a single sample chamber.

According to an aspect of the present invention, there is provided a microfluidic device having a center of rotation which comprises a sample chamber accommodating a sample, a first sample distribution unit connected to the sample chamber and receiving the sample, a sample transfer unit connected to the first sample distribution unit and forming a path for transferring the sample, and comprising a first connection unit connected to the first sample distribution unit and a second connection unit, wherein the distance from the center of rotation to the second connection unit is greater than the distance from the center of rotation to the first connection unit, a second sample distribution unit connected to the second connection unit and receiving the sample transferred via the sample transfer unit after filling the first sample distribution unit, and first and second analysis units respectively connected to the first and second sample distribution units and analyzing ingredients of the sample.

Each of the second connection unit, the second sample distribution unit, and the second analysis unit is provided in a plurality thereof, and the distances of the second connection units from the center of rotation increase as the second connection units are positioned farther from the first connection unit.

The microfluidic device further comprises an excess sample chamber connected to the second sample distribution unit connected to an end portion of the sample transfer unit and accommodating an excess sample.

Each of the first and second sample distribution units has a predetermined volume for metering the amount of the sample.

The volume of the first sample distribution unit is different from that of the second sample distribution.

At least one of the first and second sample distribution units comprises a supernatant collection unit accommodating supernatant of the sample obtained by centrifugation and a sediment collection unit accommodating a sediment.

Each of the first and second analysis units comprises a dilution chamber accommodating a dilution buffer to dilute the sample and a reaction chamber in which a reaction between a sample dilution buffer and a reagent is generated.

The first and second analysis units dilute the sample at different dilution ratios.

According to an aspect of the present invention, there is provided a microfluidic device which comprises a sample chamber accommodating a sample, a plurality of analysis units analyzing ingredients of the sample, a plurality of sample distribution units receiving the sample from the sample chamber and supplying the sample to the plurality of analysis units, and a sample transfer unit provided between the plurality of sample distribution units and forming a path for transferring the sample by connecting the adjoining sample distribution units, wherein the sample distribution unit that is closest to the sample chamber is directly connected to the sample chamber so that the plurality of sample distribution units are sequentially filled with the sample.

The microfluidic device having a center of rotation, wherein the plurality of sample distribution units are arranged in a circumferential direction of the microfluidic device.

Each of the plurality of sample distribution units comprises a connection unit connected to the sample transfer unit, and the connection units are positioned radially further from the center of rotation as the distance between the connection units and the sample chamber increases.

The microfluidic device further comprises an excess sample chamber connected to the sample distribution unit that is positioned at an end portion of the sample transfer unit and accommodating an excess sample.

Each of the plurality of sample distribution units has a predetermined volume for metering the amount of the sample.

At least one of the plurality of sample distribution units has a different volume from the other sample distribution units.

At least one of the plurality of sample distribution units comprises a supernatant collection unit accommodating supernatant of the sample obtained by centrifugation and a sediment collection unit accommodating a sediment.

Each of the plurality of analysis units comprises a dilution chamber accommodating a dilution buffer to dilute the sample and a reaction chamber in which a reaction between a sample dilution buffer and a reagent is generated.

The plurality of analysis units dilute the sample at different dilution ratios.

BRIEF DESCRIPTION OF THE DRAWINGS

The above and/or other aspects will become apparent and more readily appreciated from the following description of the exemplary embodiments, taken in conjunction with the accompanying drawings of which.

DETAILED DESCRIPTION OF EXEMPLARY EMBODIMENTS

Figure 1:
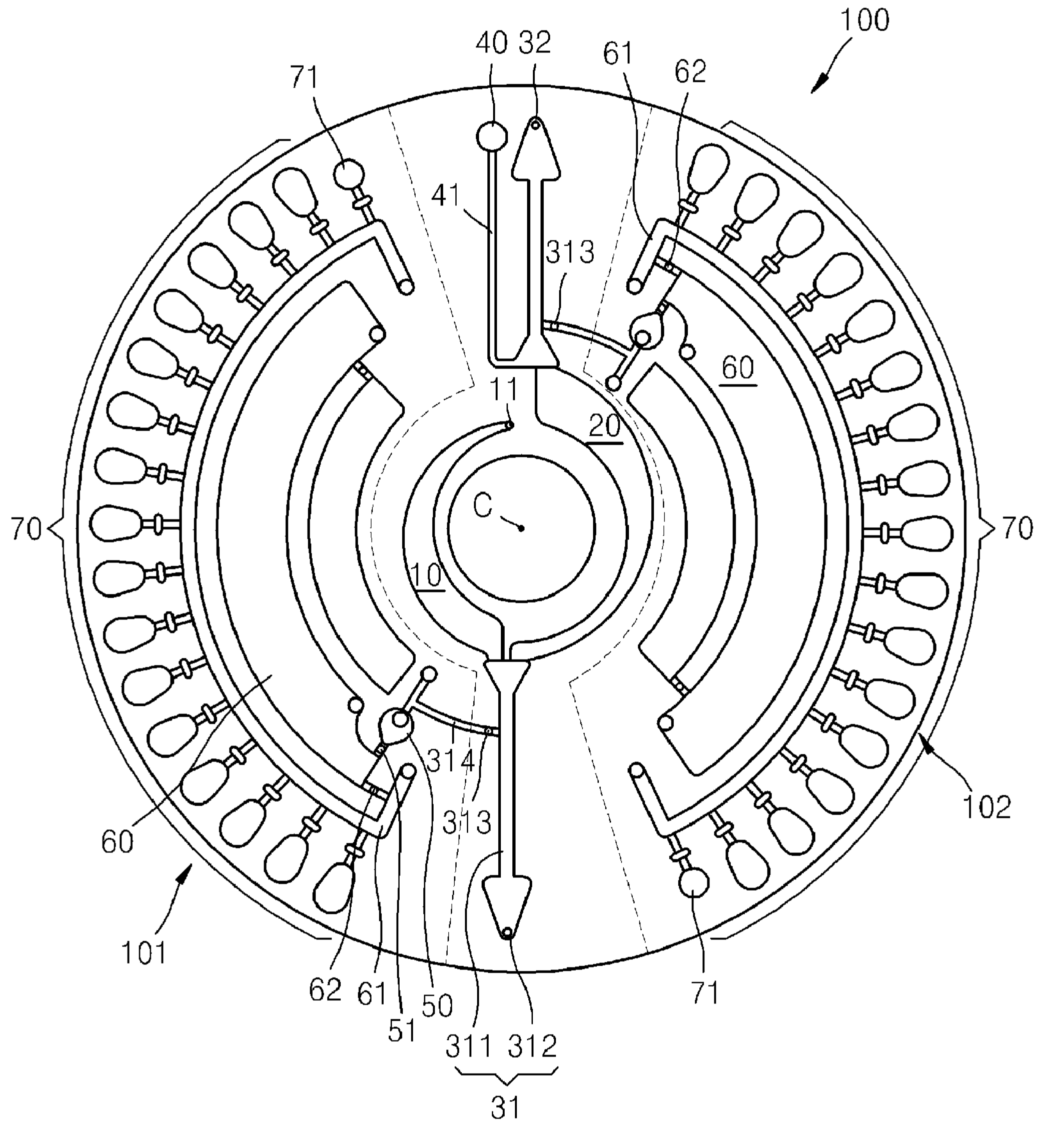
FIG. 1 is a plan view of a microfluidic device, according to an exemplary embodiment.

Reference will now be made in detail to exemplary embodiments, examples of which are illustrated in the accompanying drawings, wherein like reference numerals refer to the like elements throughout. In this regard, the present exemplary embodiments may have different forms and should not be construed as being limited to the descriptions set forth herein. Accordingly, the exemplary embodiments are merely described below, by referring to the figures, to explain aspects of the present description.

FIG. 1 is a plan view of a microfluidic device, according to an exemplary embodiment. Referring to FIG. 1, the microfluidic device according to the present exemplary embodiment includes a platform 100 that is rotatable and has the shape of, for example, a disk, and microfluidic structures providing a space for accommodating a fluid and a path for flowing the fluid, in the platform 100. The platform 100 may be rotated around a center of rotation C. That is, in the structures arranged in the platform 100, a sample may be moved and mixed due to a centrifugal force generated by the rotation of the platform 100.

Figure 2:
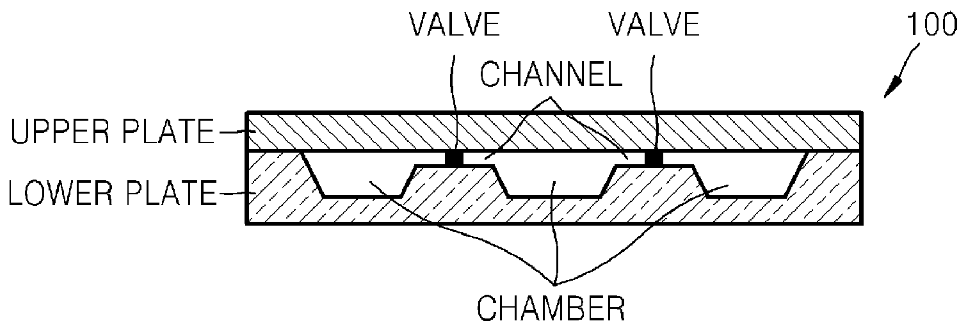
FIG. 2 is a cross-sectional view of a microfluidic device having a double-plated structure, according to an exemplary embodiment.
Figure 3:
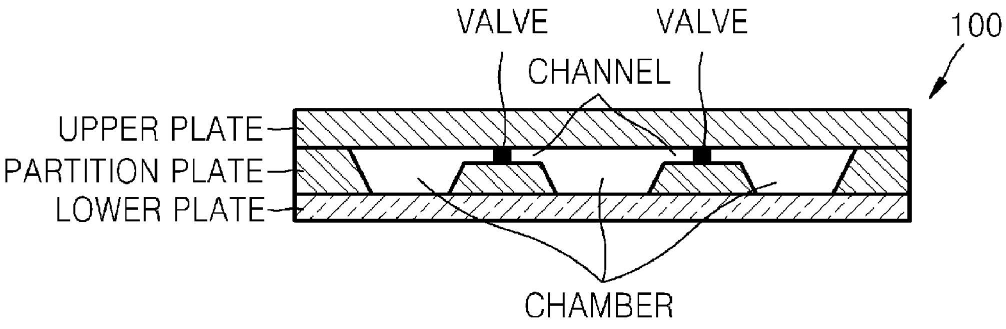
FIG. 3 is a cross-sectional view of a microfluidic device having a three-plate structure, according to an exemplary embodiment.

The platform 100 may be formed of a plastic material such as acryl or polydimethylsiloxane (PDMS) which is easily molded and has a surface that is biologically inactive. However, the platform 100 may be formed of other materials having chemical and biological stability, optical transparency, and mechanical processibility. The platform 100 may be formed of a multi-layered structure. An intaglio structure corresponding to a chamber or a channel is formed in a surface where plates contact each other and combined to provide space and paths in the platform 100. The plates may be combined using a method such as adhesion using an adhesive or double-sided adhesive tape, ultrasonic wave welding, or laser welding. For example, as illustrated in FIG. 2, the platform 100 may have a double-plated structure including a lower plate and an upper plate. Also, according to another exemplary embodiment as illustrated in FIG. 3, the platform 100 may have a partition plate for defining a space for accommodating a fluid and a path for flowing the fluid provided between the lower plate and the upper plate. The platform 100 may have a variety of shapes in addition to the above shapes.

In the microfluidic structures arranged in the platform 100, a position radially closer to the center of rotation C of the platform 100 is referred to as the inner side while a position radially far from the center of rotation C of the platform 100 is referred to as the outer side. A sample chamber 10 for accommodating a sample is of the closest microfluidic structure to the center of rotation C. A loading hole 11 for loading a sample may be provided in the sample chamber 10. First and second sample distribution units 31 and 32 receive the sample from the sample chamber 10 and supply the sample to first and second analysis units 101 and 102. The first and second sample distribution units 31 and 32 may have, for example, a predetermined volume for metering a fixed quantity of a sample needed for a test. Since the centrifugal force generated by the rotation of the platform 100 is used to move the sample from the sample chamber 10 to the first and second sample distribution units 31 and 32, the first and second sample distribution units 31 and 32 are positioned at the outer side of the sample chamber 10. The first and second sample distribution units 31 and 32 may be arranged in a circumferential direction with respect to each other.

Figure 4:
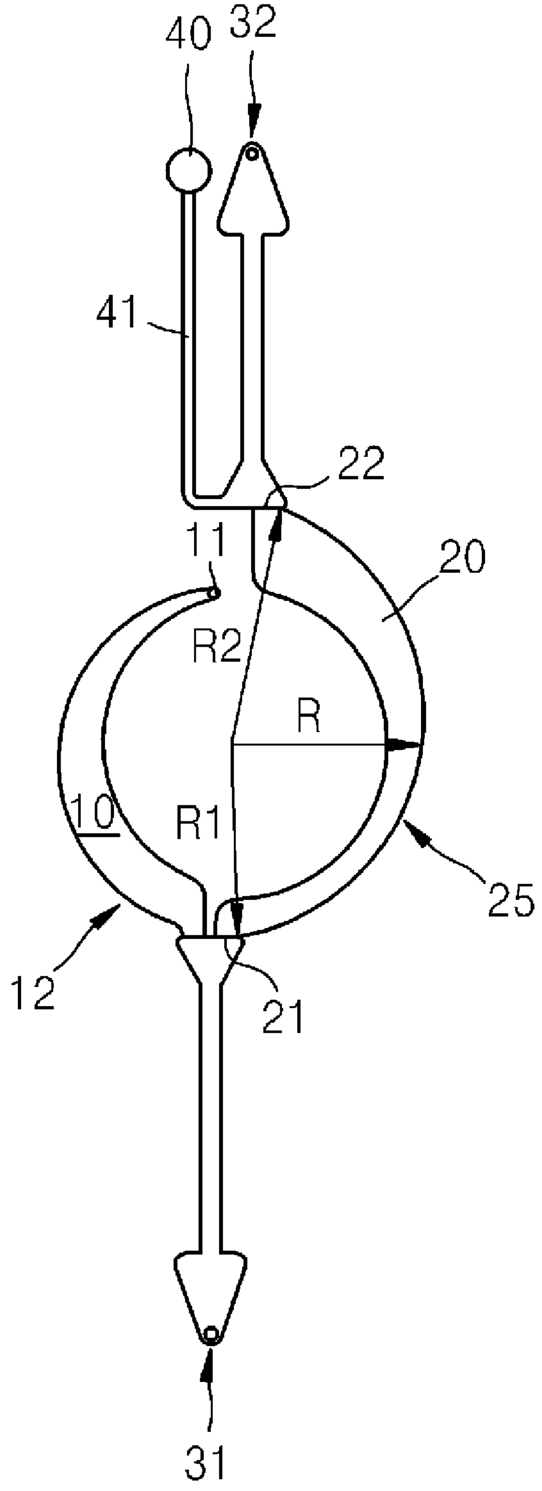
FIG. 4 illustrates in detail a sample transfer unit and a sample distribution unit of FIG. 1, according to an exemplary embodiment.

At least one of the first and second sample distribution units 31 and 32 may have a structure to centrifugally separate a sample. For example, the first sample distribution unit 31 may work as a centrifuge for separating supernatant and sediment from a sample, for example, blood, using the rotation of the platform 100. The first sample distribution unit 31 for centrifugation may have a variety of shapes, and an example thereof is illustrated in FIGS. 1 and 4. The first sample distribution unit 31 may include a supernatant collection unit 311 having a channel shape extending outwardly in a radial direction and a sediment collection unit 312 located at an end portion of the supernatant collection unit 311 to provide a space for collection of a sediment having a relatively large specific gravity. According to the above structure, a test item that is required to be centrifuged and a test item that is not required to be centrifuged may be tested using a single microfluidic device.

The first sample distribution unit 31 is directly connected to the sample chamber 10 to receive a sample. The second sample distribution unit 32 is connected to the first sample distribution unit 31 by a sample transfer unit 20. Accordingly, the sample is supplied from the sample chamber 10 to the first sample distribution unit 31 to fill the first sample distribution unit 31, and then is supplied by the sample transfer unit 20 to fill the second sample distribution unit 32.

Referring to FIG. 4, the sample transfer unit 20 forms a path for moving a sample and includes a first connection unit 21 connected to the first sample distribution unit 31 and a second connection unit 22 connected to the second sample distribution unit 32. The first and second connection units 21 and 22 may be provided at an outer wall 25 of the sample transfer unit 20. The radius R2 from the center of rotation C to the second connection unit 22 is greater than the radius R1 from the center of rotation C to the first connection unit 21, that is, R1<R2 in FIG. 4. Also, the radius of curvature R of the outer wall 25 between the first and second connection units 21 and 22 is not less than R1 and gradually increases from the first connection unit 21 to the second connection unit 22. According to the above structure, when the microfluidic device rotates, the sample is moved to the first sample distribution unit 31 due to the centrifugal force and fills the first sample distribution unit 31 and then is moved to the sample transfer unit 20. Then, the sample is moved along the outer wall 25 of the sample transfer unit 20 to the second sample distribution unit 32 via the second connection unit 22.

As described above, the plurality of sampling distribution units for receiving samples from a single sample chamber may alleviate inconvenience of loading the sample into each of the plurality of sample distribution units. The microfluidic device according to the present exemplary embodiment may further include an excess sample chamber 40. The excess sample chamber 40 is connected to the second sample distribution unit 32 via a channel 41. The excess sample left after filling the second sample distribution unit 32 is moved to and accommodated in the excess sample chamber 40 via the channel 41.

The first and second analysis units 101 and 102 may be units for testing items requiring different dilution ratios. For example, among the blood test items, ALB (Albumin), ALP (Alakaline Phosphatase), AMY (Amylase), BUN (Urea Nitrogen), Ca++ (calcium), CHOL (Total Cholesterol), Cl− (Chloide), CRE (Creatinine), GLU (Glucose), HDL (High-Density Lipoprotein cholesterol), K+ (Potassium), LD (Lactate Dehydrogenase), Na+ (Sodium), T-BIL (Total Bilirubin), TP (Total Protein), TRIG (Triglycerides), UA (Uric Acid) require a dilution ratio of serum:dilution buffer of 1:100. Also, ALT (alanine aminotransferase), AST (aspartate aminotransferase), CK (Creatin Kinase), D-BIL (Direct Bilirubin), GGT (Gamma Glutamyl Transferase) require a dilution ratio of serum:dilution buffer=1:20. Thus, the first analysis unit 101 may be a unit for testing the items requiring the dilution ratio of serum:dilution buffer of 1:100 and the second analysis unit 102 may be a unit for testing the items requiring the dilution ratio of serum:dilution buffer of 1:20.

The first and second analysis units 101 and 102 may test items having the same dilution ratio. Also, the first analysis unit 101 is for testing items that require centrifugation and the second analysis unit 102 is for testing items that do not require centrifugation. Since the first and second analysis units 101 and 102 have substantially the same structure, only the structure of the first analysis unit 101 will be discussed below in detail.

A sample distribution channel 314 for distributing a collected supernatant, for example, serum when blood is used as a sample, to a structure in which the next step is performed is arranged at a side of the supernatant collection unit 311. The sample distribution channel 314 is connected to the supernatant collection unit 311 via a valve 313. The position at which the sample distribution channel 314 is connected to the supernatant collection unit 311 may vary according to the amount of the sample to be distributed. That is, the amount of the sample to be distributed is dependent on the volume of a portion of the supernatant collection unit 312 that is close to the center of rotation C with respect to the valve 313. In the strict sense, when a metering chamber 50 is further provided as described later, the amount of the sample to be distributed is dependent on the volume of the metering chamber 50.

The valve 313 may be a microfluidic valve having a variety of shapes. In this regard, the valve 313 may be a capillary valve that is passively opened when a pressure exceeding a predetermined value is applied, or a valve actively operating by receiving external power or energy according to an operating signal. The valve 313 is a so-called normally closely valve that closes the sample distribution channel 314 to block the flow of a fluid before absorbing electromagnetic energy.

The valve 313 may be formed of thermoplastic resin such as COC (cyclic olefin copolymer), PMMA (polymethylmethacrylate), PC (polycarbonate), PS(polystyrene), POM (polyoxymethylene), PFA (perfluoralkoxy), PVC (polyvinylchloride), PP (polypropylene), PET (polyethylene terephthalate), PEEK (polyetheretherketone), PA (polyamide), PSU (polysulfone), or PVDF (polyvinylidene fluoride).

Also, the valve 313 may be formed of a phase transition material that is in a solid state at room temperature. The phase transition material is loaded into the sample distribution channel 314 in a molten state and then solidified to block the sample distribution channel 314. The phase transition material may be wax. When heated, the wax is melted and changes to a liquid state so that the volume of the phase transition material expands. The wax may be paraffin wax, microcrystalline wax, synthetic wax, or natural wax. The phase transition material may be gel or thermoplastic resin. The gel may be polyacrylamide, polyacrylates, polymethacrylates, or polyvinylamides.

A plurality of micro heating particles that generate heat by absorbing electromagnetic wave energy may be distributed in the phase transition material. The micro heating particles may each have a diameter of about 1 nm to 100 μm so as to freely pass through the sample distribution channel 314 that is may be about 0.1 mm deep and 1 mm wide. The micro heating particles characteristically generate heat by being quickly heated when subjected to electromagnetic wave energy supplied by, for example, a laser beam. As another characteristic, the micro heating particles are uniformly distributed throughout the phase transition material. To ensure the above characteristic, the micro heating particles may have a core having a metal ingredient and a hydrophobic surface structure. For example, the micro heating particles may have a Fe core and a molecule structure having a plurality of surfactants combined with Fe and encompassing the Fe. The micro heating particles may be kept in a state of being distributed in carrier oil. The carrier oil may be hydrophobic so that the micro heating particles having a hydrophobic surface structure may be uniformly distributed. The carrier oil in which the micro heating particles are distributed is poured to be mixed with the molten phase transition material. The mixture is loaded into the sample distribution channel 314 and solidified so that the sample distribution channel 314 may be blocked.

The micro heating particles are not limited to the above-described polymer particles and quantum dots or magnetic beads may also be employed. Also, the micro heating particles may be micro-metal oxides such as $Al_2O_3$, $TiO_2$, $Ta_2O_3$, $Fe_2O_3$, $Fe_3O_4$, or, $HfO_2$. The valve 313 does not necessarily include the micro heating particles and may be formed of only the phase transition material without the micro heating particles. At least a part of the platform 100 is transparent so that electromagnetic waves emitted from outside the platform 100 can be irradiated on the sample distribution channel 3 14.

The sample distribution channel 314 is connected to the metering chamber 50 that accommodates the supernatant separated from the sample. The metering chamber 50 is connected to a dilution chamber 60 via a valve 51. The valve 51 may be a microfluidic valve of the same type as the above-described valve 313.

The dilution chamber 60 is for providing a sample dilution buffer in which supernatant and a dilution buffer are mixed in a predetermined ratio. A predetermined amount of a dilution buffer is accommodated in the dilution chamber 60 considering the dilution ratio between the supernatant and the dilution buffer needed for the test. The metering chamber 50 may be designed to have a volume capable of accommodating the amount of sample determined considering the dilution ratio. As long as the valve 51 is kept closed, the sample of an amount exceeding the volume of the metering chamber 50 may not be input to the metering chamber 50. Accordingly, only a fixed amount of the supernatant may be supplied to the dilution chamber 60. As described above, by precisely designing the position at which the sample distribution channel 314 is connected to the supernatant collection unit 311, the sample distribution channel 314 may be directly connected to the dilution chamber 60.

A plurality of reaction chambers 70 are arranged circumferentially outside the dilution chamber 60. The reaction chambers 70 are connected to the dilution chamber 60 via a distribution channel 61. The distribution of a sample dilution buffer via the distribution channel 61 may be controlled by a valve 62. The valve 62 may be a microfluidic valve of the same type of the above-described valve 313.

The reaction chambers 70 may accommodate reagents generating different types of reactions with a sample dilution buffer. The reagents may be loaded into the reaction chambers 70 before an upper plate and a lower plate are combined to form the platform 100 during the manufacture of the microfluidic device. Also, the reaction chambers 70 may be either closed reaction chambers or reaction chambers having a vent and a loading hole. The reagents may be in a liquid state or a lyophilized solid state.

For example, reagents in a liquid state may be loaded into the reaction chambers 70 before the upper and lower plates forming the platform 100 are combined with each other during the manufacture of the microfluidic device and the reagents may be simultaneously lyophilized according to a lyophilisation program. Then, the upper and lower plates are combined to accommodate the lyophilized reagents. Also, cartridges accommodating the lyophilized reagents may be inserted into the reaction chambers 70. The lyophilized reagent may be obtained by adding a filler and a surfactant to a liquid reagent and lyophilizing the same. The filler helps the lyophilized reagent to have a porous structure and facilitates later the solution of a diluted buffer obtained by mixing the reagent and the diluted buffer input to the reaction chambers 70.

The filler may be selected from a group consisting of BSA (bovine serum albumin), PEG (polyethylene glycol), dextran, mannitol, polyalcohol, myo-inositol, citric acid, EDTA2Na (ethylene diamine tetra acetic acid disodium salt), and BRIJ-35 (polyoxyethylene glycol dodecyl ether). Of the above fillers, one or more fillers may be selected and added according to the type of the reagent. For example, the surfactant may be selected from a group consisting of polyoxyethylene, lauryl ether, octoxynol, polyethylene alkyl alcohol, nonylphenol polyethylene glycol ether; ethylene oxid, ethoxylated tridecyl alcohol, polyoxyethylene nonylphenyl ether phosphate sodium salt, and sodium dodecyl sulfate. Of the above surfactants, one or more surfactants may be selected and added according to the type of the reagent.

A detection chamber 71 is provided to determine whether a sampling diluted buffer is loaded into all of the reaction chambers 70. The detection chamber 71 does not accommodate the reagent and is provided at an end portion of the distribution channel 61. The sampling diluted buffer first fills the reaction chamber 70 that is closest to the dilution chamber 60 and the detection chamber 71 last. Thus, by checking whether the detection chamber 71 is filled with the sampling diluted buffer, it can be determined whether all of the reaction chambers 70 are filed with the sampling diluted buffer. Although not shown, an air vent for exhausting internal air may also be provided in the microfluidic device.

Figure 5:
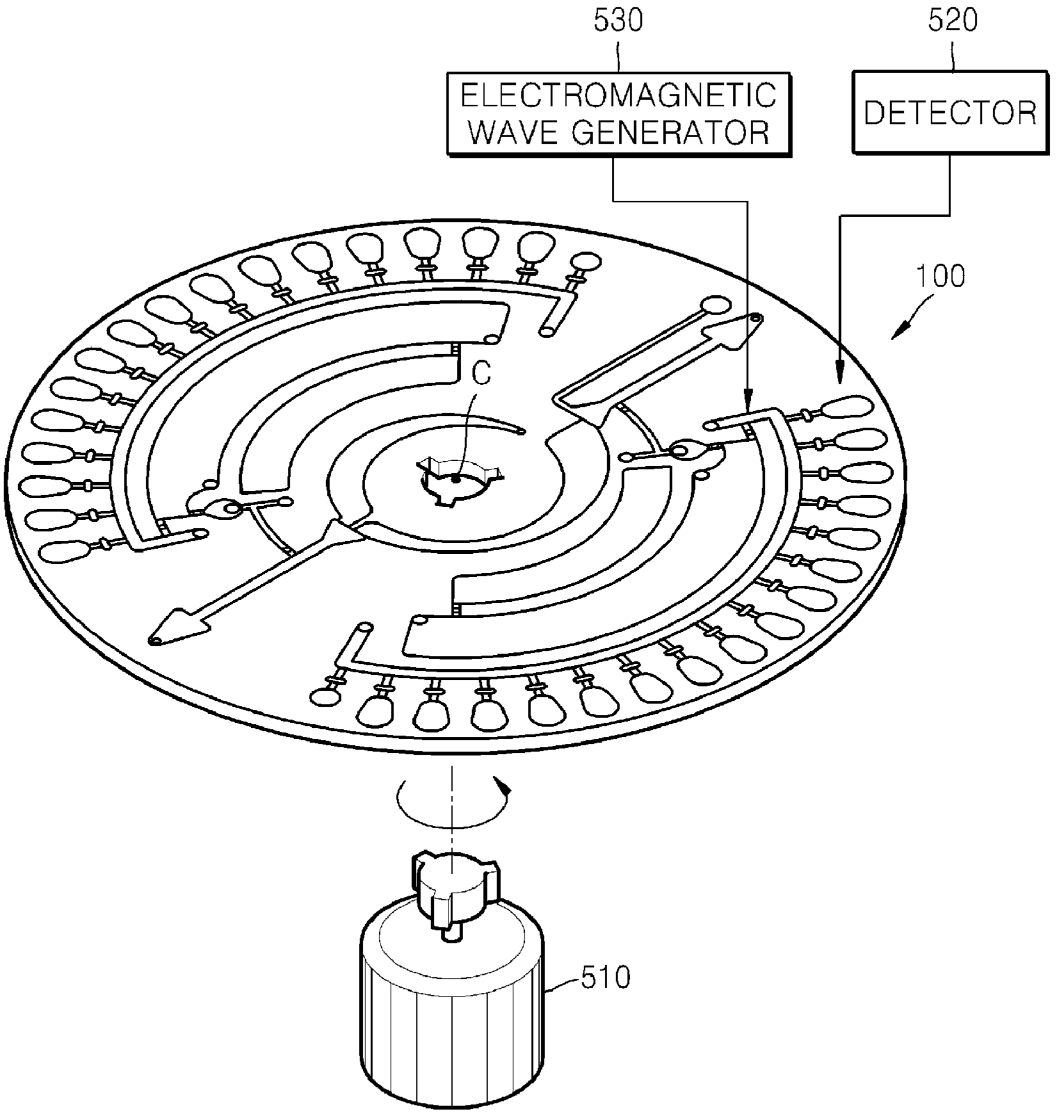
FIG. 5 is a perspective view of an analyzer using the microfluidic device of FIG. 1, according to an exemplary embodiment.

FIG. 5 is a perspective view of an analyzer using the microfluidic device of FIG. 1. Referring to FIG. 5, the analyzer includes a rotation drive unit 510 rotating the microfluidic device to move a sample to a predetermined position in the microfluidic device. Also, the rotation drive unit 510 rotates the microfluidic device to centrifuge the sample and move a separated supernatant to a predetermined position in the microfluidic device. Also, the rotation drive unit 510 stops the microfluidic device at a predetermined position so that one of the reaction chambers 70 faces a detector 520 and the valves face an electromagnetic wave generator 530. The rotation drive unit 510 may have a motor drive unit (not shown) capable of controlling an angular position of the microfluidic device. The motor drive unit may use a step motor or a DC motor. The detector 520 detects, for example, a fluorescence/illumination characteristic, and/or an optical characteristic such as light absorption, of a material to be detected. The electromagnetic wave generator 530 operates the valves by, for example, emitting a laser beam. The electromagnetic wave generator 530 may be moved in a radial direction of the microfluidic device.

In the sample analysis process using the microfluidic device, a sample is initially loaded into the sample chamber 10. A liquid dilution buffer such as a buffer solution or distilled water is loaded into the dilution chamber 60. In doing so, an appropriate amount of a dilution buffer is loaded into the dilution chamber 60 such that a dilution ratio of the sample dilution buffer may be suitable for a test item.

The microfluidic device is installed on the rotation drive unit 510 of the analyzer as illustrated in FIG. 5. The rotation drive unit 510 rotates the microfluidic device at a slow speed. The slow speed signifies a rotation speed suitable for moving the sample from the sample chamber 10 to the first and second sample distribution units 31 and 32. Then, the sample accommodated in the sample chamber 10 is moved to the first sample distribution unit 31 by a centrifugal force to fill the first sample distribution unit 31. When the first sample distribution unit 31 is completely filled with the sample, the sample is input to the sample transfer unit 20 via the first connection unit 21. Due to the centrifugal force, the sample flows along the outer wall 25 of the sample transfer unit 20 to be input to the second sample distribution unit 32 via the second connection unit 22. After completely filling the second sample distribution unit 32, the remaining sample is moved to the excess sample chamber 40 along the channel 41 and accommodated in the excess sample chamber 40.

Next, a sample analysis operation is performed. For instance, when the test item of the second analysis unit 102 does not require centrifugation, the analysis using the second analysis unit 102 may be first performed. The rotation drive unit 510 rotates the microfluidic device so that the valve 313 faces the electromagnetic wave generator 530. When electromagnetic waves are irradiated to the valve 313, the valve material forming the valve 313 is changed to a liquid state due to the energy of the electromagnetic waves, thereby opening the channel 314. The rotation drive unit 510 rotates the microfluidic device at a rotation speed at which a centrifugal separation is not generated. Then, due to the rotation of the microfluidic device, the sample accommodated in the second sample distribution unit 32 flows to the metering chamber 50 along the channel 314 due to the centrifugal force. The rotation drive unit 510 rotates the microfluidic device so that the valve 51 faces the electromagnetic wave generator 530. When electromagnetic waves are irradiated to the valve 51, the valve material forming the valve 51 is changed to a liquid state due to the energy of the electromagnetic waves, and thus the valve 51 is opened so that the sample is input to the dilution chamber 60. The rotation drive unit 510 may shake the microfluidic device to the left and right, several times, to mix the sample and the dilution buffer. Accordingly, a sample dilution buffer in which the sample and the dilution buffer are mixed is formed in the dilution chamber 60. The rotation drive unit 510 rotates the microfluidic device so that the valve 62 faces the electromagnetic wave generator 530. When electromagnetic waves are irradiated to the valve 62, the valve material forming the valve 62 is melted due to the energy of the electromagnetic waves, thereby opening the distribution channel 61. As the microfluidic device rotates, the sample dilution buffer is input to the reaction chambers 70 and the detection chamber 71 via the distribution channel 61 due to the centrifugal force. After the microfluidic device is rotated in order for the detection chamber to face the detector 520, a light absorption value of the detection chamber 71 is measured to determine whether the detection chamber 71 includes the sample dilution buffer. The reagent accommodated in the reaction chambers 70 is mixed with the sample dilution buffer. To mix the reagent and the sample dilution buffer, the rotation drive unit 510 may shake the microfluidic device to the left and right, several times, to mix the sample and the sample dilution buffer. Then, after the microfluidic device is rotated in order for the reaction chambers 70 to face the detector 520, light is irradiated to the mixture of the reagent and the sample dilution buffer so that the fluorescence/illumination characteristic, and/or an optical characteristic such as light absorption, are detected. As a result, it can be determined whether a particular material exists in the mixture and/or how large the amount of the material is.

In an operation of testing an item requiring centrifugation using the first analysis unit 101, the rotation drive unit 510 rotates the microfluidic device at a high speed. The high speed signifies a rotation speed at which the sample is centrifuged. Then, supernatant is concentrated at the supernatant collection unit 311 and a material having a heavy mass is concentrated at the sediment collection unit 3 12. The rotation drive unit 510 rotates the microfluidic device in order for the valve 313 to face the electromagnetic wave generator 530. When electromagnetic waves are irradiated to the valve 313, the valve material forming the valve 313 is melted due to the energy of the electromagnetic waves, thereby opening the channel 314. As the microfluidic device is rotated, the supernatant is moved to the metering chamber 50 along the channel 314 due to the centrifugal force. The rotation drive unit 510 rotates the microfluidic device in order for the valve 51 to face the electromagnetic wave generator 530. When electromagnetic waves are irradiated to the valve 51, the valve material forming the valve 51 is melted due to the energy of the electromagnetic waves, and thus the sample is input to the dilution chamber 60. The rotation drive unit 510 may shake the microfluidic device to the left and right, several times, to mix the supernatant and the dilution buffer. Accordingly, a sample dilution buffer in which the supernatant and the dilution buffer are mixed is formed in the dilution chamber 60. The rotation drive unit 510 rotates the microfluidic device in order for the valve 62 to face the electromagnetic wave generator 530. When electromagnetic waves are irradiated to the valve 62, the valve material forming the valve 62 is melted due to the energy of the electromagnetic waves, thereby opening the distribution channel 61. As the microfluidic device rotates, the sample dilution buffer is input to the reaction chambers 70 and the detection chamber 71 via the distribution channel 61 due to the centrifugal force. After the microfluidic device is rotated in order for the detection chamber 71 to face the detector 520, a light absorption value of the detection chamber 71 is measured to determine whether the detection chamber 71 includes the sample dilution buffer. The reagent accommodated in the reaction chambers 70 is mixed with the sample dilution buffer. To mix the reagent and the sample dilution buffer, the rotation drive unit 510 may shake the microfluidic device to the left and right, several times, to mix the sample and the sample dilution buffer. Then, after the microfluidic device is rotated in order for reaction chambers 70 to face the detector 520, light is emitted to the mixture of the reagent and the sample dilution buffer so that the fluorescence/illumination characteristic, and/or an optical characteristic such as light absorption, are detected. As a result, it can be determined whether a particular material exists in the mixture and/or how much of the material exists.

In the above-described sample analysis process, the sample required to be centrifuged is analyzed after the sample not required to be centrifuged is analyzed. However, the present invention is not limited to the above sample analysis sequence. For example, the sample may be simultaneously distributed from the sample chamber 10 to the first and second sample distribution units 31 and 32. The sample not required to be centrifuged is mixed with the dilution buffer to thus produce a first sample dilution buffer. The sample required to be centrifuged is centrifuged and the obtained supernatant is mixed with the dilution buffer to thus produce a second sample dilution buffer. Then, the first and second sample dilution buffers are moved to the detection chamber of a corresponding analysis unit and mixed with the reagent so that it may be determined whether a particular material exists in the mixture and/or how much of the material exists.

Figure 6:
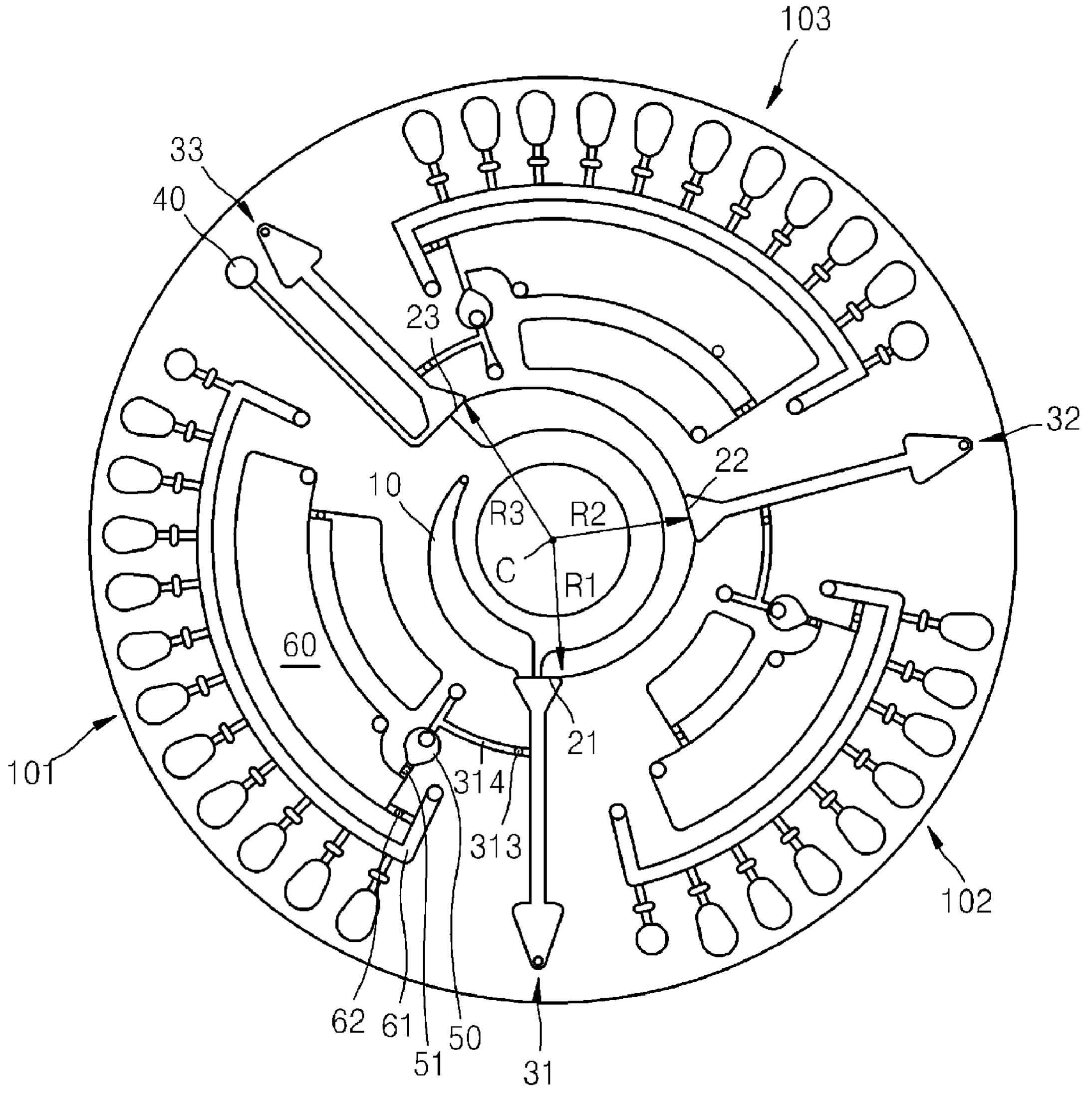
FIG. 6 is a plan view of a microfluidic device, according to another exemplary embodiment.

FIG. 6 is a plan view of a microfluidic device according to another exemplary embodiment. Referring to FIG. 6, the microfluidic device according to the present exemplary embodiment includes the first sample distribution unit 31, the first analysis unit 101, the second sample distribution unit 32, the second analysis unit 102, a third sample distribution unit 33, and a third analysis unit 103. The first, second and third sample distribution units 31, 32 and 33 are arranged in a circumferential direction. The sample transfer unit 20 includes the first connection unit 21 connected to the first sample distribution unit 31, the second connection unit 22 connected to the second sample distribution unit 32, and a third connection unit 23 connected to the third sample distribution unit 33. The radius R2 from the center of rotation C of the microfluidic device to the second connection unit 22 is greater than the radius R1 from the center of rotation C of the microfluidic device to the first connection unit 21. Also, a radius R3 from the center of rotation C of the microfluidic device to the third connection unit 23 that is relatively far from the first connection unit 21 is greater than the radius R2 from the center of rotation C of the microfluidic device to the second connection unit 22 that is relatively close to the first connection unit 21. That is, $R1<R2<R3$. The excess sample chamber 40 is connected to the third sample distribution unit 33 which is connected to the third connection unit 23 of the sample transfer unit 20. The first, second and third analysis units 101, 102 and 103 may test items requiring the same or different dilution ratios. The structure of the third analysis unit 103 may be the same as those of the first analysis unit 101 and the second analysis unit 102.

Figure 7:
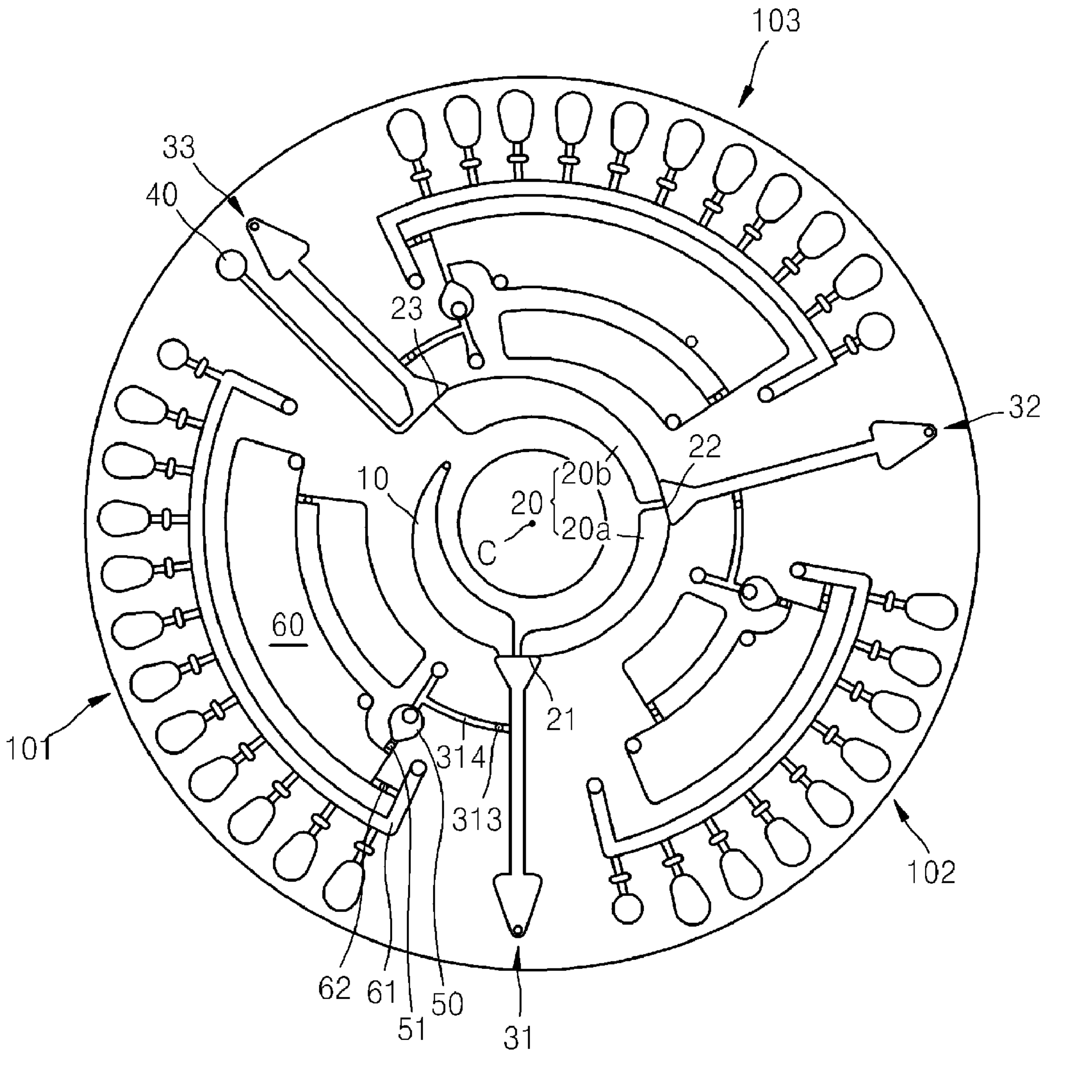
FIG. 7 is a plan view of a microfluidic device, according to another exemplary embodiment.

FIG. 7 is a plan view of a microfluidic device according to another exemplary embodiment. Referring to FIG. 7, the structure of the microfluidic device according to the present exemplary embodiment is the same as that of the microfluidic device of FIG. 6, except that the sample transfer unit 20 is divided into two sub-transfer units 20*a* and 20*b*.

Figure 8:
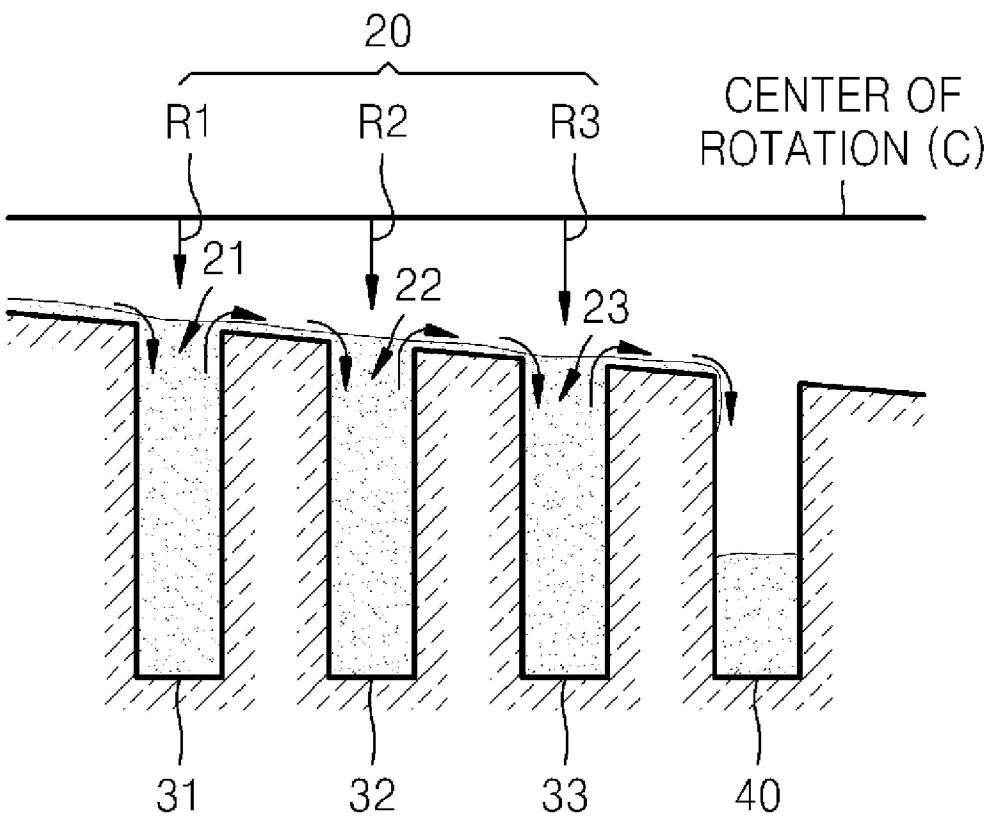
FIG. 8 illustrates the movement of a sample in the microfluidic devices illustrated in FIGS. 6 and 7, according to an exemplary embodiment.

FIG. 8 illustrates the movement of a sample in the microfluidic devices illustrated in FIGS. 6 and 7, according to an exemplary embodiment. Referring to FIG. 8, since the distances from the center of rotation C of the microfluidic device to the first, second and third connection units 21, 22, and 23 are R1, R2 and R3, respectively, wherein R1<R2<R3, the sample comes out of the sample chamber 10 and sequentially fills the first, second and third connection units 21, 22, and 23 in this order. The remaining sample is accommodated in the excess sample chamber 40.

As described above, according to the one or more exemplary embodiments, the microfluidic device may be used to analyze a variety of samples obtained from a human body and any living organisms, in addition to blood. Also, although two or three sample distribution units and analysis units are provided in the above-described exemplary embodiments, the present invention is not limited thereto and four or more sample distribution units and analysis units may be provided if necessary.

It should be understood that the exemplary embodiments described therein should be considered in a descriptive sense only and not for purposes of limitation. Descriptions of features or aspects within each exemplary embodiment should typically be considered as available for other similar features or aspects in other exemplary embodiments.

What is claimed is:

1. A microfluidic device comprising:

a sample chamber which accommodates a sample;

a first sample distribution unit which is connected to the sample chamber and receives the sample from the sample chamber;

a second sample distribution unit;

a sample transfer unit having an outer wall with a radius of curvature which provides a path for transferring the sample from the first sample distribution unit to the second sample distribution after the first sample distribution unit is filled with the sample, the sample transfer unit comprising a first connection unit which is connected to the first sample distribution unit and a second connection unit which is connected to the second sample distribution unit, wherein a distance from a center of rotation of the microfluidic device to the second connection unit is greater than a distance from the center of rotation to the first connection unit, and the radius of curvature of the outer wall between the first and second connection units gradually increases from the first connection unit to the second connection unit;

a first analysis unit which is connected to the first sample distribution unit and analyzes ingredients of the sample received from the first sample distribution unit; and a second analysis unit which is connected to the second sample distribution unit and analyzes ingredients of the sample received from the second sample distribution unit.

2. The microfluidic device of claim 1, further comprising:

a third sample distribution unit; and a third analysis unit, wherein the sample transfer unit provides a path for transferring the sample from the second sample distribution unit to the third sample distribution after the second sample distribution unit is filled with the sample, the sample transfer unit further comprises a third connection unit which is connected to the third sample distribution unit, a distance of the third connection unit from the center of rotation is greater than the distance from the center of rotation to the second connection unit, the third analysis unit which is connected to the third sample distribution unit and analyzes the ingredients of the sample received from the third sample distribution unit, and an excess sample chamber is connected to the third sample distribution unit, and receives and accommodates an excess sample after the third sample distribution unit is filled with the sample.

3. The microfluidic device of claim 1, further comprising an excess sample chamber which is connected to the second sample distribution unit, and receives and accommodates an excess sample after the second sample distribution unit is filled with the sample.

4. The microfluidic device of claim 1, wherein each of the first and second sample distribution units has a predetermined volume for metering an amount of the sample.

5. The microfluidic device of claim 4, wherein the volume of the first sample distribution unit is different from the volume of the second sample distribution.

6. The microfluidic device of claim 1, wherein at least one of the first and second sample distribution units comprises:

a supernatant collection unit which accommodates supernatant of the sample obtained by centrifugation; and a sediment collection unit which accommodates a sediment.

7. The microfluidic device of claim 1, wherein each of the first and second analysis units comprises:

a dilution chamber which accommodates a dilution buffer to dilute the sample; and a reaction chamber in which a reaction between a sample dilution buffer and a reagent is generated.

8. The microfluidic device of claim 1, wherein the first and second analysis units dilute the sample at different dilution ratios.

9. A microfluidic device comprising:

a sample chamber which accommodates a sample;

a plurality of analysis units which analyze ingredients of the sample;

a plurality of sample distribution units which receive the sample from the sample chamber and supply the sample to the plurality of analysis units; and a sample transfer unit having an outer wall with a radius of curvature which is disposed between the plurality of sample distribution units and provides a path for transferring the sample between adjoining sample distribution units, wherein a sample distribution unit that is closest to the sample chamber is directly connected to the sample chamber so that the plurality of sample distribution units are sequentially filled with the sample beginning with the sample distribution unit that is closest to the sample chamber, and the radius of curvature of the outer wall between the plurality of sample distribution units gradually increases from the sample distribution unit closest to the sample chamber to each sequential sample distribution unit.

10. The microfluidic device of claim 9, wherein the plurality of sample distribution units are arranged in a circumferential direction of the microfluidic device with respect to a center of rotation of the microfluidic device.

11. The microfluidic device of claim 10, wherein the sample transfer unit comprises a plurality of connection units connected to the plurality of sample distribution units, respectively, and the connection units are sequentially positioned radially further from the center of rotation as a distance between the connection units and the sample chamber increases.

12. The microfluidic device of claim 9, further comprising an excess sample chamber which is connected to a sample distribution unit that is positioned at an end portion of the sample transfer unit, and receives and accommodates an excess sample after the sample distribution unit that is positioned at the end portion of the sample transfer unit is filled with the sample.

13. The microfluidic device of claim 9, wherein each of the plurality of sample distribution units has a predetermined volume for metering an amount of the sample.

14. The microfluidic device of claim 13, wherein at least one of the plurality of sample distribution units has a different volume from the other sample distribution units.

15. The microfluidic device of claim 9, wherein at least one of the plurality of sample distribution units comprises:

a supernatant collection unit which accommodates supernatant of the sample obtained by centrifugation; and a sediment collection unit which accommodates a sediment.

16. The microfluidic device of claim 9, wherein each of the plurality of analysis units comprises:

a dilution chamber which accommodates a dilution buffer to dilute the sample; and a reaction chamber in which a reaction between a sample dilution buffer and a reagent is generated.

17. The microfluidic device of claim 9, wherein the plurality of analysis units dilute the sample at different dilution ratios.

18. A microfluidic device comprising:

a sample chamber which accommodates a sample;

a plurality of sample distribution units which are sequentially disposed in a circumferential direction around a center of rotation of the microfluidic device, wherein a first sample distribution unit of the plurality of sample distribution units is connected to and receives the sample from the sample chamber; and a sample transfer unit having an outer wall with a radius of curvature which is connected to the plurality of distribution units and sequentially transfers the sample from the first sample distribution unit to other ones of the plurality of distribution units due to rotation of the microfluidic device, wherein a distance from each of the plurality of sample distribution units to the center of rotation of the microfluidic device increases in the circumferential direction so that first sample distribution unit is closest to the center of rotation and a last sample distribution is farthest from the center of rotation, and the radius of curvature of the outer wall between the plurality of sample distribution units gradually increases from the first sample distribution unit to each sequential sample distribution unit.

19. The microfluidic device of claim 18, wherein a width of the sample transfer unit increases in the circumferential direction as the sample transfer unit extends from the first sample distribution unit.

20. The microfluidic device of claim 18, further comprising a plurality of analysis units which are connected to the plurality of sample distribution units and analyze ingredients of the sample received from the plurality of sample distribution units, each of the plurality analysis units comprising a plurality of reaction chambers disposed in the circumferential direction around the center of rotation of the microfluidic device.

* * * * *